(12) United States Patent
Merlet et al.

(10) Patent No.: US 8,580,287 B2
(45) Date of Patent: Nov. 12, 2013

(54) OIL-BASED AGROCHEMICAL COMPOSITIONS WITH INCREASED VISCOSITY

(75) Inventors: Stéphanie Merlet, La Celle sur Morin (FR); William Lamarca, Cregy les Meaux (FR); Ludwig Schieferstein, Ratingen (DE); Markus Scherer, Köln (DE); Peter Bene, Köln (DE)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 13/201,721

(22) PCT Filed: Feb. 6, 2010

(86) PCT No.: PCT/EP2010/000752
§ 371 (c)(1),
(2), (4) Date: Aug. 16, 2011

(87) PCT Pub. No.: WO2010/094408
PCT Pub. Date: Aug. 26, 2010

(65) Prior Publication Data
US 2011/0301037 A1 Dec. 8, 2011

(30) Foreign Application Priority Data
Feb. 17, 2009 (EP) .................... 09002181

(51) Int. Cl.
*A01N 25/00* (2006.01)
(52) U.S. Cl.
USPC ..................... 424/405; 504/116.1

(58) Field of Classification Search
None
See application file for complete search history.

(56) References Cited

U.S. PATENT DOCUMENTS 6,329,324 B1 * 12/2001 Brueggemann et al. ...... 504/363
2004/0170660 A1    9/2004 Wendel et al.

FOREIGN PATENT DOCUMENTS

| | | |
|---|---|---|
| CA | 2168947 | 2/1995 |
| DE | 19936223 | 2/2001 |
| EP | 0498231 | 8/1992 |
| EP | 498231 | * 8/1992 |
| EP | 1762221 | 3/2007 |
| WO | WO 92/01377 | 2/1992 |
| WO | WO 9201377 | * 2/1992 |
| WO | WO 95/05402 | 2/1995 |
| WO | WO 03/020232 | 3/2003 |
| WO | WO 2007/093295 | 8/2007 |
| WO | WO 2007/093297 | 8/2007 |

OTHER PUBLICATIONS

"Machine Translation of EP1762221", Mar. 14, 2007, 12 pages.
"Machine Translation of WO2007/093295", Aug. 23, 2007, 16 pages.
"Machine Translation of WO2007/093297", Aug. 23, 2007, 16 pages.
"PCT International Search Report for PCT/EP2010/000752", Jul. 26, 2010, 5 pages.

* cited by examiner

*Primary Examiner* — Alton Pryor
(74) *Attorney, Agent, or Firm* — Servilla Whitney LLC

(57) ABSTRACT

Suggested are oil-based agrochemical compositions with increased viscosity, comprising (a) biocides, (b) hydrophobic carriers, and (c) polymers selected from the group consisting of poly(meth)acrylates, polymaleates and polyfumarates.

17 Claims, 1 Drawing Sheet

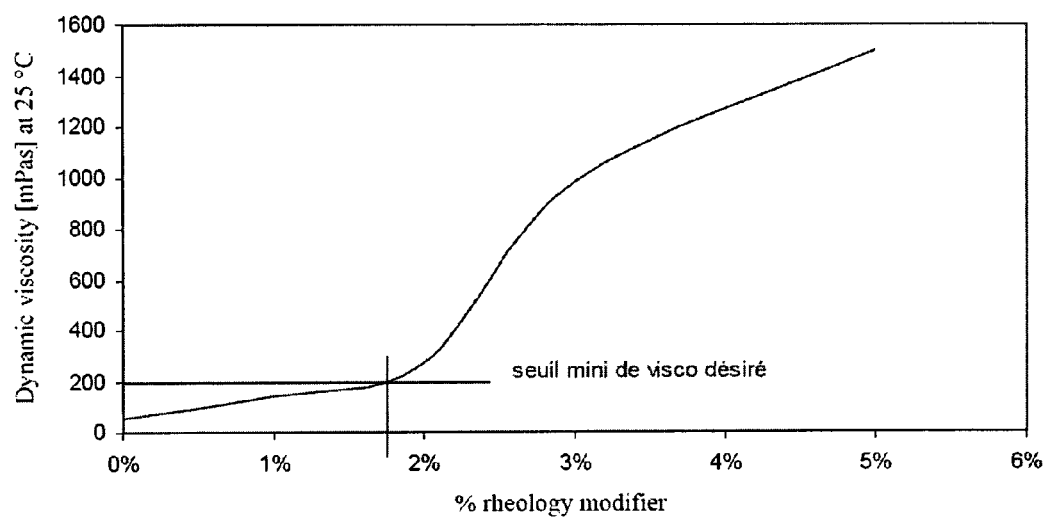
Dynamic viscosity of rape seed oil as a function of rheology modifier concentration

OIL-BASED AGROCHEMICAL COMPOSITIONS WITH INCREASED VISCOSITY

CROSS-REFERENCE TO RELATED APPLICATIONS

This application is the National Stage entry of PCT/EP2010/000752, filed on Feb. 6, 2010, which claims priority to European Patent application number 09002181.7 filed on Feb. 17, 2009, both of which are incorporated herein by reference in their entireties.

FIELD OF THE INVENTION

The present invention is related to the area of agrochemicals and covers oil-based compositions comprising biocides and certain polymers suitable for increasing the viscosity.

BACKGROUND OF THE INVENTION

A large number of substantially water insoluble biocidal and agrochemical active substances are used extensively for controlling pests and/or for promoting the healthy growth of crops and livestock. For this purpose it is usually necessary or preferred to apply them in a fluid and preferably a diluted form exhibiting a viscosity sufficient to remain as droplets on the leaves in order to penetrate, but not too high that spraying becomes difficult.

Reference is made for example to WO 95/005402 A1 assigned to BASF disclosing aqueous copolymer dispersions are obtained by radical initiated copolymerisation or by copolymerisation initiated by the use of ionising radiation of: (A) 40 to 99% by weight of one or several water-insoluble, monoethylenically unsaturated monomers; (B) 1 to 60% by weight of one or several water-soluble, monoethylenically unsaturated monomers; and (C) 0 to 30% by weight of one or several ethylenically polyunsaturated monomers, in an aqueous medium in the presence of 2 to 20% by weight, in relation to the total monomer amount, of surface active compounds as emulsifiers. These dispersions have a mean particle size from 5 to 37 nm as determined by light scattering in the aqueous medium. Such dispersions are suitable for preparing varnishes, paints and adhesives, as film-builders in hair-care cosmetic compositions, as protective media against ultraviolet light and as carriers for substances contained in pharmaceuticals, cosmetics or agrochemicals. The document, however, does not disclose the use of polyacrylates for increasing the viscosity of compositions comprising biocides and oil bodies.

A major issue for pesticides dispersions in oil carriers is the stability of the formulation during storage: pesticides particles tend to settle and separate over time and/or temperature variations leading to non homogeneous products. The pesticide formulation should therefore exhibit a moderate viscosity of about 500 to about 1000 mPa·s to prevent settling during storage but also should become rather fluid when submitted to mechanical energy (mixing, stress . . . ) for a better handling by the end-users. To obtain such defined viscosity behaviour the use of rheology modifiers is necessary.

The object of the present invention has been to design new rheology modifiers able to provide the appropriate rheological behaviour to oil-based biocide compositions.

SUMMARY OF THE INVENTION

One aspect of the invention relates to an oil-based agrochemical composition with increased viscosity, comprising (a) one or more biocides, (b) one or more hydrophobic carriers, and (c) one or more polymers selected from the group consisting of poly(meth)acrylates, polymaleates and polyfumarates. Methods of producing an agricultural composition are also provided, the method comprising using a polymer selected from the group consisting of poly(meth)acrylates, polymaleates and polyfumarates as a rheology modifier for making agricultural compositions. A detailed method is provided where viscosity of a hydrophobic carrier for an agricultural composition is increased, the method comprising: adding a polymer selected from the group consisting of poly(meth)acrylates, polymaleates, and polyfumarates to the hydrophobic carrier to form a mixture; wherein the mixture has a higher viscosity than the hydrophobic carrier.

DETAILED DESCRIPTION OF THE INVENTION

The present invention refers to oil-based agrochemical compositions with increased viscosity, comprising
biocides,
hydrophobic carriers, and
polymers selected from the group consisting of poly(meth)acrylates, polymaleates and polyfumarates.

Surprisingly it has been observed that adding said defined polymers even in small amounts results in a significant increase in viscosity of oil based biocide compositions which remain stable even in case of serious changes in temperature (−5 to 60° C.) and stay fluid even by introduction of energy (e.g. stirring).

Biocides

A biocide is a chemical substance capable of killing different forms of living organisms used in fields such as medicine, agriculture, forestry, and mosquito control. Usually, biocides are divided into two sub-groups:
pesticides, which includes fungicides, herbicides, insecticides, algicides, moluscicides, miticides and rodenticides, and
antimicrobials, which includes germicides, antibiotics, antibacterials, antivirals, antifungals, antiprotozoals and antiparasites.

Biocides can also be added to other materials (typically liquids) to protect the material from biological infestation and growth. For example, certain types of quaternary ammonium compounds (quats) can be added to pool water or industrial water systems to act as an algicide, protecting the water from infestation and growth of algae.

Pesticides

The U.S. Environmental Protection Agency (EPA) defines a pesticide as "any substance or mixture of substances intended for preventing, destroying, repelling, or mitigating any pest". A pesticide may be a chemical substance or biological agent (such as a virus or bacteria) used against pests including insects, plant pathogens, weeds, mollusks, birds, mammals, fish, nematodes (roundworms) and microbes that compete with humans for food, destroy property, spread disease or are a nuisance. In the following examples, pesticides suitable for the agrochemical compositions according to the present invention are given:

Fungicides. A fungicide is one of three main methods of pest control—the chemical control of fungi in this case. Fungicides are chemical compounds used to prevent the spread of fungi in gardens and crops. Fungicides are also used to fight fungal infections. Fungicides can either be contact or systemic. A contact fungicide kills fungi when sprayed on its surface. A systemic fungicide has to be absorbed by the fungus before the fungus dies. Examples for suitable fungicides, according to the present invention, encompass the following species: (3-ethoxypropyl)mercury bromide, 2-methoxyethylmercury chloride, 2-phenylphenol, 8-hydroxyquinoline sulfate, 8-phenylmercurioxyquinoline, acibenzolar, acylamino acid fungicides, acypetacs, aldimorph, aliphatic nitrogen fungicides, allyl alcohol, amide fungicides, ampropylfos, anilazine, anilide fungicides, antibiotic fungicides, aromatic fungicides, aureofungin, azaconazole, azithiram, azoxystrobin, barium polysulfide, benalaxyl benalaxyl-M, benodanil, benomyl, benquinox, bentaluron, benthiavalicarb, benzalkonium chloride, benzamacril, benzamide fungicides, benzamorf, benzanilide fungicides, benzimidazole fungicides, benzimidazole precursor fungicides, benzimidazolylcarbamate fungicides, benzohydroxamic acid, benzothiazole fungicides, bethoxazin, binapacryl, biphenyl, bitertanol, bithionol, blasticidin-S, Bordeaux mixture, boscalid, bridged diphenyl fungicides, bromuconazole, bupirimate, Burgundy mixture, buthiobate, butylamine, calcium polysulfide, captafol, captan, carbamate fungicides, carbamorph, carbanilate fungicides, carbendazim, carboxin, carpropamid, carvone, Cheshunt mixture, chinomethionat, chlobenthiazone, chloraniformethan, chloranil, chlorfenazole, chlorodinitronaphthalene, chloroneb, chloropicrin, chlorothalonil, chlorquinox, chlozolinate, ciclopirox, climbazole, clotrimazole, conazole fungicides, conazole fungicides (imidazoles), conazole fungicides (triazoles), copper (II) acetate, copper(II) carbonate, basic, copper fungicides, copper hydroxide, copper naphthenate, copper oleate, copper oxychloride, copper(II) sulfate, copper sulfate, basic, copper zinc chromate, cresol, cufraneb, cuprobam, cuprous oxide, cyazofamid, cyclafuramid, cyclic dithiocarbamate fungicides, cycloheximide, cyflufenamid, cymoxanil, cypendazole, cyproconazole, cyprodinil, dazomet, DBCP, debacarb, decafentin, dehydroacetic acid, dicarboximide fungicides, dichlofluanid, dichlone, dichlorophen, dichlorophenyl, dicarboximide fungicides, dichlozoline, diclobutrazol, diclocymet, diclomezine, dicloran, diethofencarb, diethyl pyrocarbonate, difenoconazole, diflumetorim, dimethirimol, dimethomorph, dimoxystrobin, diniconazole, dinitrophenol fungicides, dinobuton, dinocap, dinocton, dinopenton, dinosulfon, dinoterbon, diphenylamine, dipyrithione, disulfiram, ditalimfos, dithianon, dithiocarbamate fungicides, DNOC, dodemorph, dodicin, dodine, DONATODINE, drazoxolon, edifenphos, epoxiconazole, etaconazole, etem, ethaboxam, ethirimol, ethoxyquin, ethylmercury 2,3-dihydroxypropyl mercaptide, ethylmercury acetate, ethylmercury bromide, ethylmercury chloride, ethylmercury phosphate, etridiazole, famoxadone, fenamidone, fenaminosulf, fenapanil, fenarimol, fenbuconazole, fenfuram, fenhexamid, fenitropan, fenoxanil, fenpiclonil, fenpropidin, fenpropimorph, fentin, ferbam, ferimzone, fluazinam, fludioxonil, flumetover, flumorph, fluopicolide, fluoroimide, fluotrimazole, fluoxastrobin, fluquinconazole, flusilazole, flusulfamide, flutolanil, flutriafol, folpet, formaldehyde, fosetyl, fuberidazole, furalaxyl, furametpyr, furamide fungicides, furanilide fungicides, furcarbanil, furconazole, furconazole-cis, furfural, furmecyclox, furophanate, glyodin, griseofulvin, guazatine, halacrinate, hexachlorobenzene, hexachlorobutadiene, hexachlorophene, hexaconazole, hexylthiofos, hydrargaphen, hymexazol, imazalil, imibenconazole, imidazole fungicides, iminoctadine, inorganic fungicides, inorganic mercury fungicides, iodomethane, ipconazole, iprobenfos, iprodione, iprovalicarb, isoprothiolane, isovaledione, kasugamycin, kresoxim-methyl, lime sulphur, mancopper, mancozeb, maneb, mebenil, mecarbinzid, mepanipyrim, mepronil, mercuric chloride, mercuric oxide, mercurous chloride, mercury fungicides, metalaxyl, metalaxyl-M, metam, metazoxolon, metconazole, methasulfocarb, methfuroxam, methyl bromide, methyl isothiocyanate, methylmercury benzoate, methylmercury dicyandiamide, methylmercury pentachlorophenoxide, metiram, metominostrobin, metrafenone, metsulfovax, milneb, morpholine fungicides, myclobutanil, myclozolin, N-(ethylmercury)-p-toluenesulphonanilide, nabam, natamycin, nitrostyrene, nitrothal-isopropyl, nuarimol, OCH, octhilinone, ofurace, organomercury fungicides, organophosphorus fungicides, organotin fungicides, orysastrobin, oxadixyl, oxathiin fungicides, oxazole fungicides, oxine copper, oxpoconazole, oxycarboxin, pefurazoate, penconazole, pencycuron, pentachlorophenol, penthiopyrad, phenylmercuriurea, phenylmercury acetate, phenylmercury chloride, phenylmercury derivative of pyrocatechol, phenylmercury nitrate, phenylmercury salicylate, phenylsulfamide fungicides, phosdiphen, phthalide, phthalimide fungicides, picoxystrobin, piperalin, polycarbamate, polymeric dithiocarbamate fungicides, polyoxins, polyoxorim, polysulfide fungicides, potassium azide, potassium polysulfide, potassium thiocyanate, probenazole, prochloraz, procymidone, propamocarb, propiconazole, propineb, proquinazid, prothiocarb, prothioconazole, pyracarbolid, pyraclostrobin, pyrazole fungicides, pyrazophos, pyridine fungicides, pyridinitril, pyrifenox, pyrimethanil, pyrimidine fungicides, pyroquilon, pyroxychlor, pyroxyfur, pyrrole fungicides, quinacetol, quinazamid, quinconazole, quinoline fungicides, quinone fungicides, quinoxaline fungicides, quinoxyfen, quintozene, rabenzazole, salicylanilide, silthiofam, simeconazole, sodium azide, sodium orthophenylphenoxide, sodium pentachlorophenoxide, sodium polysulfide, spiroxamine, streptomycin, strobilurin fungicides, sulfonanilide fungicides, sulfur, sultropen, TCMTB, tebuconazole, tecloftalam, tecnazene, tecoram, tetraconazole, thiabendazole, thiadifluor, thiazole fungicides, thicyofen, thifluzamide, thiocarbamate fungicides, thiochlorfenphim, thiomersal, thiophanate, thiophanate-methyl, thiophene fungicides, thioquinox, thiram, tiadinil, tioxymid, tivedo, tolclofos-methyl, tolnaftate, tolylfluanid, tolylmercury acetate, triadimefon, triadimenol, triamiphos, triarimol, triazbutil, triazine fungicides, triazole fungicides, triazoxide, tributyltin oxide, trichlamide, tricyclazole, tridemorph, trifloxystrobin, triflumizole, triforine, triticonazole, unclassified fungicides, undecylenic acid, uniconazole, urea fungicides, validamycin, valinamide fungicides, vinclozolin, zarilamid, zinc naphthenate, zineb, ziram, zoxamide and their mixtures.

Herbicides. An herbicide is a pesticide used to kill unwanted plants. Selective herbicides kill specific targets while leaving the desired crop relatively unharmed. Some of these act by interfering with the growth of the weed and are often based on plant hormones. Herbicides used to clear waste ground are nonselective and kill all plant material with which they come into contact. Herbicides are widely used in agriculture and in landscape turf management. They are applied in total vegetation control (TVC) programs for maintenance of highways and railroads. Smaller quantities are used in forestry, pasture systems, and management of areas set aside as wildlife habitat. In the following, a number of suitable herbicides are compiled:

2,4-D, a broadleaf herbicide in the phenoxy group used in turf and in no-till field crop production. Now mainly used in a blend with other herbicides that act as synergists, it is the most widely used herbicide in the world, third most commonly used in the United States. It is an example of synthetic auxin (plant hormone).

Atrazine, a triazine herbicide used in corn and sorghum for control of broadleaf weeds and grasses. It is still used because of its low cost and because it works as a synergist when used with other herbicides, it is a photosystem II inhibitor.

Clopyralid, a broadleaf herbicide in the pyridine group, used mainly in turf, rangeland, and for control of noxious thistles. Notorious for its ability to persist in compost. It is another example of synthetic auxin.

Dicamba, a persistent broadleaf herbicide active in the soil, used on turf and field corn. It is another example of synthetic auxin.

Glyphosate, a systemic nonselective (it kills any type of plant) herbicide used in no-till burndown and for weed control in crops that are genetically modified to resist its effects. It is an example of a EPSPs inhibitor.

Imazapyr, a non-selective herbicide used for the control of a broad range of weeds including terrestrial annual and perennial grasses and broadleaved herbs, woody species, and riparian and emergent aquatic species.

Imazapic, a selective herbicide for both the pre- and post-emergent control of some annual and perennial grasses and some broadleaf weeds. Imazapic kills plants by inhibiting the production of branched chain amino acids (valine, leucine, and isoleucine), which are necessary for protein synthesis and cell growth.

Metoalachlor, a pre-emergent herbicide widely used for control of annual grasses in corn and sorghum; it has largely replaced atrazine for these uses.

Paraquat, a nonselective contact herbicide used for no-till burndown and in aerial destruction of marijuana and coca plantings. More acutely toxic to people than any other herbicide in widespread commercial use.

Picloram, a pyridine herbicide mainly used to control unwanted trees in pastures and edges of fields. It is another synthetic auxin.

Triclopyr.

Insecticides. An insecticide is a pesticide used against insects in all developmental forms. They include ovicides and larvicides used against the eggs and larvae of insects. Insecticides are used in agriculture, medicine, industry and the household. In the following, suitable insecticides are mentioned:

Chlorinated insecticides such as, for example, Camphechlor, DDT, Hexachlorocyclohexane, gamma-Hexachlorocyclohexane, Methoxychlor, Pentachlorophenol, TDE, Aldrin, Chlordane, Chlordecone, Dieldrin, Endosulfan, Endrin, Heptachlor, Mirex and their mixtures;

Organophosphorus compounds such as, for example, Acephate, Azinphos-methyl, Bensulide, Chlorethoxyfos, Chlorpyrifos, Chlorpyriphos-methyl, Diazinon, Dichlorvos (DDVP), Dicrotophos, Dimethoate, Disulfoton, Ethoprop, Fenamiphos, Fenitrothion, Fenthion, Fosthiazate, Malathion, Methamidophos, Methidathion, Methyl-parathion, Mevinphos, Naled, Omethoate, Oxydemeton-methyl, Parathion, Phorate, Phosalone, Phosmet, Phostebupirim, Pirimiphos-methyl, Profenofos, Terbufos, Tetrachlorvinphos, Tribufos, Trichlorfon and their mixture;

Carbamates such as, for example, Aldicarb, Carbofuran, Carbaryl, Methomyl, 2-(1-Methylpropyl)phenyl methylcarbamate and their mixtures;

Pyrethroids such as, for example, Allethrin, Bifenthrin, Deltamethrin, Permethrin, Resmethrin, Sumithrin, Tetramethrin, Tralomethrin, Transfluthrin and their mixtures;

Plant toxin derived compounds such as, for example, Derris (rotenone), Pyrethrum, Neem (Azadirachtin), Nicotine, Caffeine and their mixtures.

Rodenticides. Rodenticides are a category of pest control chemicals intended to kill rodents. Rodents are difficult to kill with poisons because their feeding habits reflect their place as scavengers. They would eat a small bit of something and wait, and if they do not get sick, they would continue eating. An effective rodenticide must be tasteless and odorless in lethal concentrations, and have a delayed effect. In the following, examples for suitable rodenticides are given:

Anticoagulants are defined as chronic (death occurs after 1-2 weeks post ingestion of the lethal dose, rarely sooner), single-dose (second generation) or multiple dose (first generation) cumulative rodenticides. Fatal internal bleeding is caused by lethal dose of anticoagulants such as brodifacoum, coumatetralyl or warfarin. These substances in effective doses are antivitamins K, blocking the enzymes $K_1$-2,3-epoxide-reductase (this enzyme is preferentially blocked by 4-hydroxycoumarin/4-hydroxythiacoumarin derivatives) and $K_1$-quinone-reductase (this enzyme is preferentially blocked by indandione derivatives), depriving the organism of its source of active vitamin $K_1$. This leads to a disruption of the vitamin K cycle, resulting in an inability of production of essential blood-clotting factors (mainly coagulation factors II (prothrombin), VII (proconvertin), IX (Christmas factor) and X (Stuart factor)). In addition to this specific metabolic disruption, toxic doses of 4-hydroxycoumarin/4-hydroxythiacoumarin and indandione anticoagulants are causing damage to tiny blood vessels (capillaries), increasing their permeability, causing diffuse internal bleedings (haemorrhagias). These effects are gradual; they develop in the course of days and are not accompanied by any nociceptive perceptions, such as pain or agony. In the final phase of intoxication the exhausted rodent collapses in hypovolemic circulatory shock or severe anemia and dies calmly. Rodenticidal anticoagulants are either first generation agents (4-hydroxycoumarin type: warfarin, coumatetralyl; indandione type: pindone, diphacinone, chlorophacinone), generally requiring higher concentrations (usually between 0.005 and 0.1%), consecutive intake over days in order to accumulate the lethal dose, poor active or inactive after single feeding and less toxic than second generation agents, which are derivatives of 4-hydroxycoumarin (difenacoum, brodifacoum, bromadiolone and flocoumafen) or 4-hydroxy-1-benzothiin-2-one (4-hydroxy-1-thiacoumarin, sometimes incorrectlly referred to as 4-hydroxy-1-thiocoumarin, for reason see heterocyclic compounds), namely difethialone. Second generation agents are far more toxic than first generation agents, they are generally applied in lower concentrations in baits (usually in the order of 0.001-0.005%), and are lethal after single ingestion of bait and are effective also against strains of rodents that have become resistant against first generation anticoagulants; thus the second generation anticoagulants are sometimes referred to as "superwarfarins". Sometimes, anticoagulant rodenticides are potentiated by an antibiotic, most commonly by sulfaquinoxaline. The aim of this association (e.g. warfarin 0.05%+sulfaquinoxaline 0.02%, or difenacoum 0.005%+sulfaquinoxaline 0.02% etc.) is that the antibiotic/bacteriostatic agent suppresses intestinal/gut symbiotic microflora that represents a source of vitamin K. Thus the symbiotic bacteria are killed or their metabolism is impaired and the production of vitamin K by them is diminuted, an effect which logically contributes to the action of anticoagulants. Antibiotic agents other than sulfaquinoxaline may be used, for example co-trimoxazole, tetracycline, neomycin or metronidazole. A further synergism used in rodenticidal baits is that of an association of an anticoagulant with a compound with vitamin D-activity, i.e. cholecalciferol or ergocalciferol (see below). A typical formula used is, e.g., warfarin 0.025-0.05%+cholecalciferol 0.01%. In some countries there are even fixed three-component rodenticides, i.e. anticoagulant+antibiotic+vitamin D, e.g. difenacoum 0.005%+sulfaquinoxaline 0.02%+cholecalciferol 0.01%. Associations of a second-generation anticoagulant with an antibiotic and/or vitamin D are considered to be effective even against the most resistant strains of rodents, though some second generation anticoagulants (namely brodifacoum and difethialone), in bait concentrations of 0.0025-0.005% are so toxic that no known resistant strain of rodents exists and even rodents resistant against any other derivatives are reliably exterminated by application of these most toxic anticoagulants.

Vitamin $K_1$ has been suggested and successfully used as an antidote for pets or humans, which/who were either accidentally or intentionally (poison assaults on pets, suicidal attempts) exposed to anticoagulant poisons. In addition, since some of these poisons act by inhibiting liver functions and in progressed stages of poisoning, several blood-clotting factors as well as the whole volume of circulating blood lacks, a blood transfusion (optionally with the clotting factors present) can save a person's life who inadvertently takes them, which is an advantage over some older poisons.

Metal phosphides have been used as a means of killing rodents and are considered single-dose fast acting rodenticides (death occurs commonly within 1-3 days after single bait ingestion). A bait consisting of food and a phosphide (usually zinc phosphide) is left where the rodents can eat it. The acid in the digestive system of the rodent reacts with the phosphide to generate the toxic phosphine gas. This method of vermin control has possible use in places where rodents are resistant to some of the anticoagulants, particularly for control of house and field mice; zinc phosphide baits are also cheaper than most second-generation anticoagulants, so that sometimes, in cases of large infestation by rodents, their population is initially reduced by copious amounts of zinc phosphide bait applied, and the rest of the population that survived the initial fast-acting poison is then eradicated by prolonged feeding on anticoagulant bait. Inversely, the individual rodents that survived anticoagulant bait poisoning (rest population) can be eradicated by pre-baiting them with nontoxic bait for a week or two (this is important to overcome bait shyness, and to get rodents used to feeding in specific areas by offering specific food, especially when eradicating rats) and subsequently applying poisoned bait of the same sort as used for pre-baiting until all consumption of the bait ceases (usually within 2-4 days). These methods of alternating rodenticides with different modes of action provides a factual or an almost 100% eradication of the rodent population in the area if the acceptance/palatability of bait is good (i.e., rodents readily feed on it).

Phosphides are rather fast acting rat poisons, resulting in that the rats are dying usually in open areas instead of the affected buildings. Typical examples are aluminum phosphide (fumigant only), calcium phosphide (fumigant only), magnesium phosphide (fumigant only) and zinc phosphide (in baits). Zinc phosphide is typically added to rodent baits in amounts of around 0.75-2%. The baits have a strong, pungent garlic-like odor characteristic for phosphine liberated by hydrolysis. The odor attracts (or, at least, does not repulse) rodents, but has a repulsive effect on other mammals; birds, however (notably wild turkeys), are not sensitive to the smell and feed on the bait thus becoming collateral damage.

Hypercalcemia. Calciferols (vitamins D), cholecalciferol (vitamin $D_3$) and ergocalciferol (vitamin $D_2$) are used as rodenticides, which are toxic to rodents for the same reason that they are beneficial to mammals: they are affecting calcium and phosphate homeostasis in the body. Vitamins D are essential in minute quantities (few IUs per kilogram body weight daily, which is only a fraction of a milligram), and like most fat soluble vitamins they are toxic in larger doses as they readily result in the so-called hypervitaminosis, which is, simply said, poisoning by the vitamin. If the poisoning is severe enough (that is, if the dose of the toxicant is high enough), it eventually leads to death. In rodents consuming the rodenticidal bait it causes hypercalcemia by raising the calcium level, mainly by increasing calcium absorption from food, mobilising bone-matrix-fixed calcium into ionised form (mainly monohydrogencarbonate calcium cation, partially bound to plasma proteins, $[CaHCO_3]^+$), which circulates dissolved in the blood plasma, and after ingestion of a lethal dose the free calcium levels are raised sufficiently so that blood vessels, kidneys, the stomach wall and lungs are mineralised/calcificated (formation of calcificates, crystals of calcium salts/complexes in the tissues thus damaging them), leading further to heart problems (myocard is sensitive to variations of free calcium levels that are affecting both myocardial contractibility and excitation propagation between atrias and ventriculas) and bleeding (due to capillary damage) and possibly kidney failure. It is considered to be single-dose, or cumulative (depending on concentration used; the common 0.075% bait concentration is lethal to most rodents after a single intake of larger portions of the bait), sub-chronic (death occurring usually within days to one week after ingestion of the bait). Applied concentrations are 0.075% cholecalciferol and 0.1% ergocalciferol when used alone. There is an important feature of calciferols toxicology which is that they are synergistic with anticoagulant toxicants. This means that mixtures of anticoagulants and calciferols in the same bait are more toxic than the sum of toxicities of the anticoagulant and the calciferol in the bait so that a massive hypercalcemic effect can be achieved by a substantially lower calciferol content in the bait and vice-versa. More pronounced anticoagulant/hemorrhagic effects are observed if calciferol is present. This synergism is mostly used in baits low in calciferol because effective concentrations of calciferols are more expensive than effective concentrations of most anticoagulants. The historically very first application of a calciferol in rodenticidal bait was, in fact, the Sorex product Sorexa® D (with a different formula than today's Sorexa® D) back in the early 1970's, containing warfarin 0.025%+ergocalciferol 0.1%. Today, Sorexa® CD contains a 0.0025% difenacoum+0.075% cholecalciferol combination. Numerous other brand products containing either calciferols 0.075-0.1% (e.g. Quintox®, containing 0.075% cholecalciferol) alone, or a combination of calciferol 0.01-0.075% with an anticoagulant are marketed.

Miticides, moluscicides and nematicides. Miticides are pesticides that kill mites. Antibiotic miticides, carbamate miticides, formamidine miticides, mite growth regulators, organochlorine, permethrin and organophosphate miticides all belong to this category. Molluscicides are pesticides used to control mollusks, such as moths, slugs and snails. These substances include metaldehyde, methiocarb and aluminium sulfate. A nematicide is a type of chemical pesticide used to kill parasitic nematodes (a phylum of worm). A nematicide is obtained from a neem tree's seed cake; which is the residue of neem seeds after oil extraction. The neem tree is known by several names in the world but was first cultivated in India since ancient times.

Antimicrobials. In the following examples, antimicrobials suitable for agrochemical compositions according to the present invention are given. Bactericidal disinfectants mostly used are those applying active chlorine (i.e., hypochlorites, chloramines, dichloroisocyanurate and trichloroisocyanurate, wet chlorine, chlorine dioxide, etc.), active oxygen (peroxides such as peracetic acid, potassium persulfate, sodium perborate, sodium percarbonate and urea perhydrate), iodine (iodpovidone (povidone-iodine, Betadine), Lugol's solution, iodine tincture, iodinated nonionic surfactants), concentrated alcohols (mainly ethanol, 1-propanol, called also n-propanol and 2-propanol, called isopropanol and mixtures thereof; further, 2-phenoxyethanol and 1- and 2-phenoxypropanols are used), phenolic substances (such as phenol (also called "carbolic acid"), cresols (called "Lysole" in combination with liquid potassium soaps), halogenated (chlorinated, brominated) phenols, such as hexachlorophene, triclosan, trichlorophenol, tribromophenol, pentachlorophenol, Dibromol and salts thereof), cationic surfactants such as some quaternary ammonium cations (such as benzalkonium chloride, cetyl trimethylammonium bromide or chloride, didecyldimethylammonium chloride, cetylpyridinium chloride, benzethonium chloride) and others, non-quarternary compounds such as chlorhexidine, glucoprotamine, octenidine dihydrochloride, etc.), strong oxidizers such as ozone and permanganate solutions;

heavy metals and their salts such as colloidal silver, silver nitrate, mercury chloride, phenylmercury salts, copper sulfate, copper oxide-chloride etc. Heavy metals and their salts are the most toxic and environmentally hazardous bactericides and, therefore, their use is strongly suppressed or forbidden; further, also properly concentrated strong acids (phosphoric, nitric, sulfuric, amidosulfuric, toluenesulfonic acids) and alcalis (sodium, potassium, calcium hydroxides) between pH <1 or >13, particularly below elevated temperatures (above 60° C.) kill bacteria.

As antiseptics (i.e., germicide agents that can be used on human or animal body, skin, mucoses, wounds and the like), few of the above mentioned disinfectants can be used under proper conditions (mainly concentration, pH, temperature and toxicity toward man/animal). Among them, important are Some properly diluted chlorine preparations (e.g. Daquin's solution, 0.5% sodium or potassium hypochlorite solution, pH-adjusted to pH 7-8, or 0.5-1% solution of sodium benzenesulfochloramide (chloramine B)), some iodine preparations such as iodopovidone in various galenics (ointments, solutions, wound plasters), in the past also Lugol's solution, peroxides as urea perhydrate solutions and pH-buffered 0.1-0.25% peracetic acid solutions, alcohols with or without antiseptic additives, used mainly for skin antisepsis, weak organic acids such as sorbic acid, benzoic acid, lactic acid and salicylic acid some phenolic compounds such as hexachlorophene, triclosan and Dibromol, and cation-active compounds such as 0.05-0.5% benzalkonium, 0.5-4% chlorhexidine, 0.1-2% octenidine solutions.

Bactericidal antibiotics kill bacteria; bacteriostatic antibiotics only slow down their growth or reproduction. Penicillin is a bactericide, as are cephalosporins. Aminoglycosidic antibiotics can act in both a bactericidic manner (by disrupting cell wall precursor leading to lysis) or bacteriostatic manner (by connecting to 30s ribosomal subunit and reducing translation fidelity leading to inaccurate protein synthesis). Other bactericidal antibiotics according to the present invention include the fluoroquinolones, nitrofurans, vancomycin, monobactams, co-trimoxazole, and metronidazole. The preferred biocides are selected from the group consisting of oxyfluorfen, glyphosate, tebucanozol, desmedipham, phenmedipham, ethofumesat and their mixtures.

Hydrophobic Carriers

Basically, the phrase hydrophobic carriers (component b) encompass all kinds of oil bodies or oil components, in particular vegetable oils like e.g. rape seed oil, sunflower oil, soy oil, olive oil and the like, modified vegetable oils e.g. alkoxylated sunflower or soy oil, synthetic (tri)glycerides like e.g. technical mixtures of mono, di and triglycerides of $C_6$-$C_{22}$ fatty acids, fatty acid alkyl esters e.g. methyl or ethyl esters of vegetable oils (Agnique® ME 18 RD-F, Agnique® ME 18 SD-F, Agnique® ME 12C-F, Agnique® ME1270, all products of Cognis GmbH, Germany) fatty acid alkyl esters based on said $C_6$-$C_{22}$ fatty acids, mineral oils and their mixtures. Examples illustrating the nature of suitable hydrophobic carriers without limiting the invention to these examples are: Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol (Synative® ES EHK, Synative® ES EHO), esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, di-caprylyl ether (Cetiol® OE), ring-opening products of epoxidized fatty acid esters with polyols, silicone oils (cyclomethicones, silicone methicone grades, etc.), aliphatic or naphthenic hydrocarbons, such as, for example, squalane, squalene or dialkylcyclohexanes, and/or mineral oils.

Polymers

The polymers according to the present invention (component c) represent homo- or copolymers of acrylic acid esters, methacrylic acid esters, maleic acid esters or fumaric acid esters following formulas (Ia) and (Ib)

$$CH_2=CHR^1—COOR^2 \quad (Ia)$$

$$R^2OOC—CH=CH—COOR^2 \quad (Ib)$$

in which $R^1$ represents either hydrogen or methyl and $R^2$ stands for a linear or branched alkyl or alkenyl radical having 1 to 22 carbon atoms.

Alk(en)yl component. Typical examples are poly(meth) acrylates, polymaleates and polyfumaerates in which the alk (en)yl component represents methyl, ethyl, propyl or butyl or is derived from $C_6$-$C_{22}$ fatty alcohols, as for example capryl alcohol, 2-ethylhexyl alcohol, $C_8$-$C_{10}$ fatty alcohol, lauryl alcohol, myristyl alcohol, cetyl alcohol, stearyl alcohol, isostearyl alcohol, Oleyl alcohol, elaidyl alcohol, linolyl alcohol, conjugated linolyl alcohol, linoleyl alcohol, ricinolyl alcohol, 12-hydroxystearyl alcohol, gadoleayl alcohol, arachidonyl alcohol, behenyl alcohol, eruciyl alcohol and their mixtures. Particularly preferred are polyesters, comprising short ($C_6$-$C_{14}$) and/or long chain ($C_{16}$-$C_{22}$) fatty alcohols, for example esters obtained from 2-ethylhexyl alcohol and behenyl alcohol. For mixed polyesters the ratio by weight between different alcohols in the alk(en)yl moiety may vary between about 10:90 and about 90:10, preferably about 25:75 to about 75:25 and more preferably about 40:60 to about 60:40.

Acyl component. So as the alcohol moiety may comprise mixtures of different species, so can the acyl group. The ratio by weight between different unsaturated acids in the acyl moiety may vary between 10:90 and 90:10, preferably 25:75 to 75:25 and more preferably 40:60 to 60:40. It is possible to derive the polymers for example from mixtures of acrylic acid and methacrylic acid or mixtures of maleic acid and fumaric acid. In this context the polymers may also represent esters of mixtures of different unsaturated acids and different alcohols, for example poly-2-ethylhexyl/behenyl-polyacrylate/methacrylate or poly-lauryl/behenyl-maleate/fumarate. In total most preferred are the following species: Poly($C_{12/14}$)—($C_{16/18}$)-alkyl-methacrylate, Polylaurylbehenylacrylate, Poly-2-ethylhexylbehenylfumarate and Polybehenylfumarate.

Polyesters. The polyesters can be obtained according to the standards method known in organic chemistry. Typically, the polymerisation is initiated by a radical starter, for example a persulfate. It is possible, to prepare the esters in a first step followed by polymerisation or vice versa, that means first preparing the polymeric backbone and than esterifying the polymer thus obtained. The polymerisation step can be done in water emulsion or in oil/hydrophobic carrier. As far as polymaleates and polyfumerates are concerned the preferred average molecular weights are found in the range of about 5,000 to about 20,000, more preferable between about 7,000 and about 13,000 Dalton. The preferred average molecular weights for poly(meth)acrylates are considered to be much higher, typically between about 100,000 and about 500,000, preferably about 200,000 to about 300,000 Dalton.

Agricultural Compositions

In a preferred embodiment the agricultural compositions according to the present invention comprise:

(a) about 5 to about 50% b.w., preferably about 15 to about 35% b.w. biocides;

(b) about 10 to about 90% b.w., preferably about 20 to about 75% b.w. hydrophobic carriers, (c) about 0.1 to about 10% b.w., preferably about 0.5 to about 5% b.w. polymers, and (d) about 0 to about 15% b.w., preferably 1 to 10% b.w. surfactants, on condition that the amounts add with water up to 100% b.w.

Surfactants

Agricultural compositions also comprise surfactants (component d), like emulsifiers, dispersants, adjuvants normally used in Agro formulations: fatty acid derivatives, fatty alcohols, fatty alcohol polyglycolethers, phosphate esters, tristyrylphenol derivatives, alkoxylated vegetable oils/triglycerides, sorbitan esters, sorbitan ester ethoxylates, end-capped fatty alcohol polyglycol ethers, optionally alkoxylated alkyl polyglucosides and the like.

Industrial Application

Further on, additional embodiments of the present invention cover the use of polymers selected from the group consisting of poly(meth)acrylates, polymaleates and polyfumarates as rheology modifiers for making oil-based agricultural compositions. The polymers are typically added to the compositions in amounts of about 0.1 to about 5, preferably about 0.5 to about 5% b.w. calculated on the composition.

EXAMPLES

Example 1

Commercially available rape seed oil was treated with 1 to 5% b.w. (a1) polylauryl/behenylacrylate and (a2) polybehenylfumarate. Viscosity was detected according to the Brookfield method at 25° C. (spindle 1, 50 rpm). The results are shown in Table 1. FIG. 1 also illustrates the dynamic viscosity of rape seed oil after adding polylauryl/behenylacrylate.

TABLE 1

Viscosity of rape seed oil

| Rheology modifier | Viscosity [mPas] after adding modifier [% b.w.] | | | | | |
|---|---|---|---|---|---|---|
| | Control | 1.0% | 2.0% | 3.0% | 4.0% | 5.0% |
| Polylaurylbehenyl-acrylate | 51 | 140 | 270 | 980 | | 1.500 |
| Polybehenylfumarate | 50 | | 280 | 410 | 640 | gel |

Example 2

Rape seed oil methyl ester (Agnique® ME 18RD-F) was treated with up to 2.5% b.w. (b1) polybehenylfumarate and (b2) polybehenyl/2-ethylhexylfumarate. Viscosity was detected according to the Brookfield method at 25° C. (spindle 1, 50 rpm). The results are shown in Table 2.

TABLE 2

Viscosity of rape seed methyl ester

| Rheology modifier | Viscosity [mPas] after adding modifier [% b.w.] | | | | |
|---|---|---|---|---|---|
| | Control | 2.0% | 2.5% | 3.0% | 4.0% |
| Polybehenylfumarate | 20 | 85 | | 240 | 520 |
| Polybehenyl-2-ethylhexylfumarate | 20 | | 350 | | |

Example 3

Commercially available white oil was treated with up to 7% b.w. (c1) poly(12/14)-(16/18)-methacrylate and (c2) polybehenylfumarate. Viscosity was detected according to the Brookfield method at 25° C. (spindle 1, 50 rpm). The results are shown in Table 3.

TABLE 3

Viscosity of white oil

| Rheology modifier | Viscosity [mPas] after adding modifier [% b.w.] | | | | |
|---|---|---|---|---|---|
| | Control | 1.0% | 2.0% | 3.0% | 7.0% |
| Poly($C_{12/14}$)-($C_{16/18}$)-alkyl-methacrylate | 50 | | | | 700 |
| Polybehenylfumarate | 50 | 50 | 1.170 | >2.000 | |

What is claimed is:

1. An oil-based agrochemical composition with increased viscosity, comprising
   (a) 5 to 50% b.w. of one or more biocides,
   (b) 10 to 80% b.w. of one or more hydrophobic carriers, and
   (c) a non-aqueous dispersion comprising one or more polymers selected from the group consisting of poly(meth)acrylates, polymaleates and polyfumarates in an amount of 0.1 to 10% b.w. of the composition and
   (d) 0 to 15% b.w. one or more surfactants;
   wherein the amounts add with water up to 100% b.w.
   wherein the oil-based agricultural composition remains stable upon change in temperature in the range of −5° C. to 60° C. and remains fluid upon introduction of energy.

2. The oil-based agrochemical composition according to claim 1, wherein said one or more biocides (component a) are selected from the group consisting of herbicides, insecticides, fungicides and their mixtures.

3. The oil-based agrochemical composition according to claim 1, wherein said one or more hydrophobic carriers (component b) are selected from the group consisting of vegetable oils, synthetic triglycerides, fatty acid alkyl esters, mineral oils, white oils and their mixtures.

4. The oil-based agrochemical composition according to claim 1, wherein said one or more polymers comprise homo- or co-polymers of acrylic acid esters, methacrylic acid esters, maleic acid esters or fumaric acid esters following formulas (Ia) and (Ib)

$$CH_2=CHR^1-COOR^2 \quad (Ia)$$

$$R^2OOC-CH=CH-COOR^2 \quad (Ib)$$

in which $R^1$ comprises either hydrogen or methyl and $R^2$ stands for a linear or branched alkyl or alkenyl radical having 1 to 22 carbon atoms.

5. The oil-based agrochemical composition according to claim 1, wherein said one or more polymers are derived from mixtures of short ($C_6$-$C_{14}$) and long chain ($C_{16}$-$C_{22}$) fatty alcohols.

6. The oil-based agrochemical composition according to claim 1, wherein said one or more polymers are derived from mixtures of acrylic and methacrylic acid or mixtures of maleic acid and fumaric acid.

7. The oil-based agrochemical composition according to claim 1, wherein said one or more polymers comprise Poly($C_{12/14}$)-($C_{16/18}$)-alkyl-methacrylate, Polylaurylbehenylacrylate, Poly-2-ethylhexylbehenylfumarate or Polybehenylfumarate.

8. The oil-based agrochemical composition according to claim 1, wherein said one or more polymers are obtained either by esterification of the unsaturated acid with the alcohol followed by polymerisation or by polymerisation of the unsaturated acid followed by esterification.

9. The oil-based agrochemical composition according to claim 1, wherein said polymaleates and polyfumarates show an average molecular weight of 5,000 to 20,000 Dalton.

10. The oil-based agrochemical composition according to claim 1, wherein said poly(meth)acrylates show an average molecular weight of 100,000 to 500,000 Dalton.

11. A method of producing an agricultural composition, the method comprising using a non-aqueous dispersion comprising a polymer selected from the group consisting of poly(meth)acrylates, polymaleates and polyfumarates as a rheology modifier for making agricultural compositions; wherein the agricultural composition comprises;
   (a) 5 to 50% b.w. of one or more biocides,
   (b) 10 to 80% b.w. of one or more hydrophobic carriers, and
   (c) the polymer poly(meth)acrylates, polymaleates and polyfumarates in an amount of 0.1 to 10% b.w. and
   (d) 0 to 15% b.w. one or more surfactants;
   wherein the amounts add with water up to 100% b.w.
   wherein the agricultural composition remains stable upon change in temperature in the range of −5° C. to 60° C. and remains fluid upon introduction of energy.

12. The method according to claim 11, wherein said agricultural composition is a tank mix.

13. The method of claim 11, wherein the agricultural composition has a higher viscosity as compared to a comparative composition comprising the same ingredients as the agricultural composition without the presence of the one or more polymers.

14. A method of increasing viscosity of a hydrophobic carrier for an oil-based agricultural composition, the method comprising:

adding a non-aqueous dispersion comprising a polymer selected from the group consisting of poly(meth)acrylates, polymaleates, and polyfumarates to the hydrophobic carrier to form a mixture;

wherein the mixture has a higher viscosity than the hydrophobic carrier; and adding one or more biocides to the mixture to form the oil-based agricultural composition, which comprises:
(a) 5 to 50% b.w. of one or more biocides,
(b) 10 to 80% b.w. of one or more hydrophobic carriers, and
(c) the polymer poly(meth)acrylates, polymaleates and polyfumarates in an amount of 0.1 to 10% b.w. and
(d) 0 to 15% b.w one or more surfactants;
wherein the amounts add with water up to 100% b.w.;

wherein the oil-based agricultural composition remains stable upon change in temperature in the range of −5° C. to 60° C. and remains fluid upon introduction of energy.

15. The method of claim 14 wherein the oil-based agricultural composition has a viscosity in the range of 500 to 1000 mPa·s.

16. The method of claim 14, wherein said one or more polymers are derived from long chain ($C_{16}$-$C_{22}$) fatty alcohols.

17. The method of claim 16, wherein said one or more polymers are derived from mixtures of short ($C_6$-$C_{14}$) and long chain ($C_{16}$-$C_{22}$) fatty alcohols.

\* \* \* \* \*